United States Patent [19]

Palmer

[11] Patent Number: 5,718,365
[45] Date of Patent: Feb. 17, 1998

[54] PLURAL BOBBIN DISPENSER

[75] Inventor: Robert H. Palmer, Oregon City, Oreg.

[73] Assignee: Modcom, Inc., Canby, Oreg.

[21] Appl. No.: 540,258

[22] Filed: Oct. 6, 1995

[51] Int. Cl.$^6$ .................................................. B26F 3/02
[52] U.S. Cl. ............... 225/38; 225/42; 225/52; 225/89; 206/63.5; 242/594.3
[58] Field of Search ........................ 225/34, 37, 38, 225/39, 42, 52, 56, 72, 89; 206/63.5; 242/594, 594.2, 594.3, 594.5, 591, 596.1, 596.3, 598.1, 598.2; 83/650

[56] References Cited

U.S. PATENT DOCUMENTS

| | | |
|---|---|---|
| 834,790 | 10/1906 | Wolford . |
| 1,641,259 | 9/1927 | Fisher ........................... 225/34 X |
| 2,526,440 | 10/1950 | Toombs ........................ 242/594.3 |
| 2,678,777 | 5/1954 | Donkin ......................... 225/89 X |
| 2,862,676 | 12/1958 | Castelli . |
| 2,921,493 | 1/1960 | Emmert . |
| 2,999,313 | 9/1961 | Emmert . |
| 3,079,827 | 3/1963 | Castelli ......................... 225/34 X |
| 3,176,572 | 4/1965 | Comet . |
| 3,530,583 | 9/1970 | Klein et al. . |
| 3,788,175 | 1/1974 | Davis . |
| 3,903,601 | 9/1975 | Anderson et al. . |
| 4,038,753 | 8/1977 | Klein . |
| 4,217,686 | 8/1980 | Dragon . |
| 4,252,258 | 2/1981 | Plummer, III ................. 225/34 X |
| 4,330,271 | 5/1982 | Anderson . |
| 4,493,446 | 1/1985 | Wirth ........................... 225/38 X |
| 4,499,802 | 2/1985 | Simpson . |
| 4,713,001 | 12/1987 | Klein et al. . |
| 4,793,536 | 12/1988 | Urushizaki .................... 225/89 X |
| 4,944,440 | 7/1990 | Fortman ........................ 225/42 X |
| 5,016,766 | 5/1991 | Klein et al. . |
| 5,203,694 | 4/1993 | Klein . |
| 5,221,033 | 6/1993 | Klein et al. . |
| 5,280,741 | 1/1994 | Bell et al. . |
| 5,326,260 | 7/1994 | Klein et al. . |
| 5,480,084 | 1/1996 | Daniels ........................ 225/42 X |
| 5,529,490 | 6/1996 | Klein et al. ................... 206/63.5 X |

*Primary Examiner*—Eugenia Jones
*Attorney, Agent, or Firm*—Kolisch Hartwell Dickinson McCormack & Heuser

[57] ABSTRACT

In general, the medical apparatus provides contamination-free dispensing of a desired supply of cut-separable, intraoral ligators from a chain of such ligators. Preferably, the apparatus also provides quick loading/unloading of bobbins holding coil-wound chains of such ligators. More preferably, the apparatus provides easy positioning of such chains into a ready-to-use position so that a user may dispense a supply of such chain. The medical apparatus includes a frame and a bobbin around which a chain is wound. The chain preferably is elongate, homogeneous, and unitary and more preferably is a molded chain of plural cut-separable intraoral ligators (i.e., O-ring ligators) for use during an orthodontic ligating procedure. A hub structure and an anvil are attached to the frame. The hub structure includes a hub for mounting the bobbin thereon so that the bobbin rotates about the hub as the chain pays out from the bobbin. The anvil is attached to the frame such that the chain pays out from the bobbin in the direction toward the anvil. The anvil includes a blade and a resistance passageway through the anvil. The passageway is configured for the chain to be fed therethrough so that a section of chain may be severed from it by circumflecting the chain over the anvil and across the blade. Preferably, the hub structure is pivotally attached to the frame so that the bobbin may be quickly loaded and unloaded from the hub. More preferably, the anvil is also pivotally attached to the frame so that the anvil can swing up to expose the resistance passageway, thereby facilitating threading of the chain through the passageway.

12 Claims, 2 Drawing Sheets

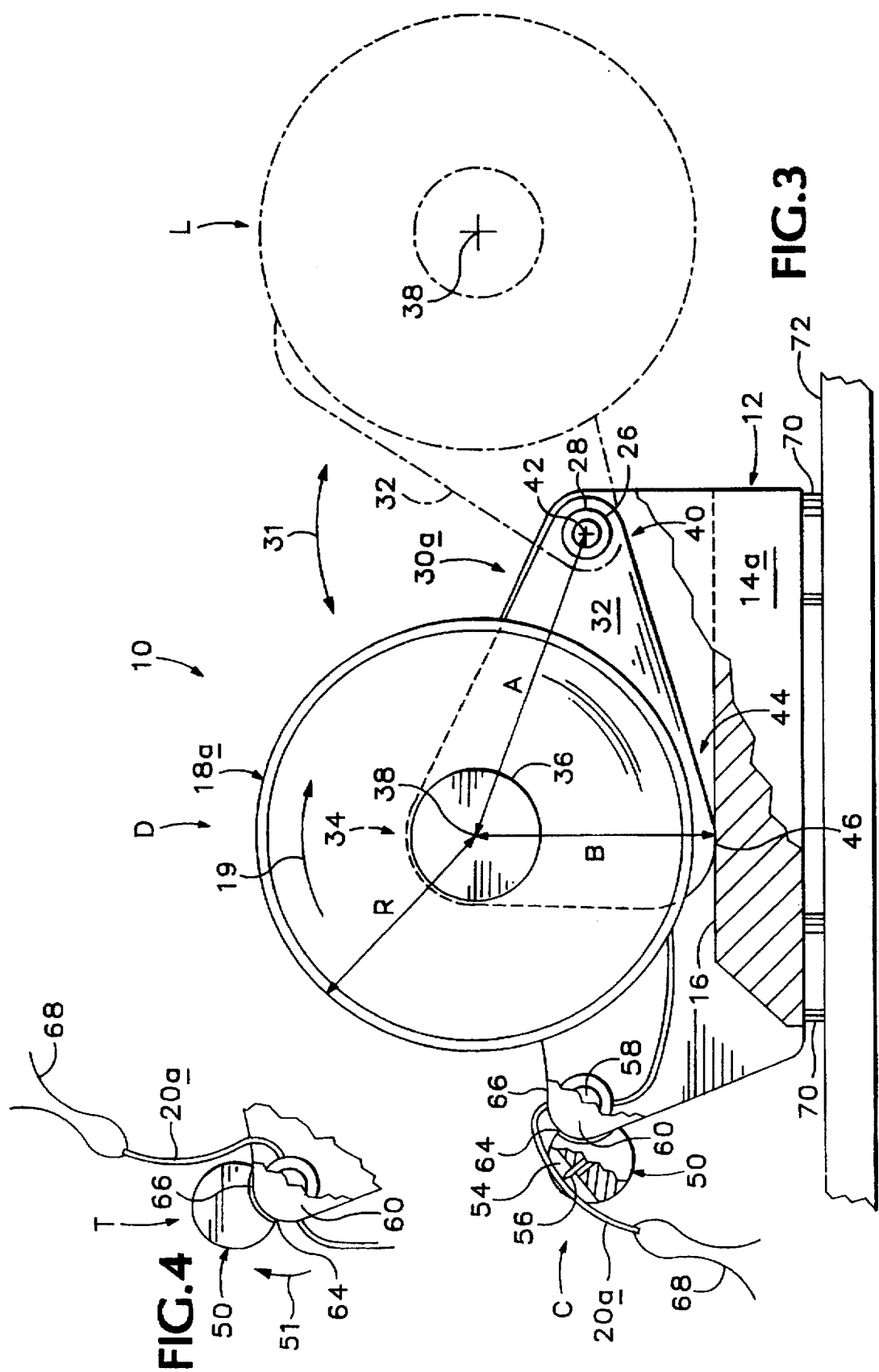

PLURAL BOBBIN DISPENSER

TECHNICAL FIELD

This invention relates generally to a chain dispensing apparatus. More particularly, this invention relates to a medical apparatus for contamination-free dispensing of a supply of cut-separable medical devices in a coil-wound chain from one or more bobbins.

BACKGROUND ART

To straighten or realign a person's teeth, a orthodontist typically affixes orthodontic devices to the person's teeth and uses tractive means with the devices to assist in tooth positioning. For many years, orthodontic practitioners have used tiny, but effective, elastomeric, orthodontic, intraoral ligators (O-rings) as tractive means for tooth positioning. Various techniques, apparatuses and arrangements have been proposed for enabling the dispensing and handling of the same. For example, known dispensing and handling techniques, apparatuses and arrangements include U.S. Pat. No. 3,903,601 to Anderson et al.; U.S. Pat. No. 4,038,753 to Klein; U.S. Pat. No. 4,330,271 to Anderson; U.S. Pat. No. 5,016,766 to Klein et al.; U.S. Pat. No. 5,221,033 to Klein et al.; and U.S. Pat. No. 5,326,260 to Klein et al.

In the dispensing and handling apparatuses proposed in the past, there are several characteristics and features which are useful and appropriate for many instances, but are not so useful and appropriate in others. For example, O-ring ligators have been presented in the past (1) as completely free ligators which are plucked from a container holding the same; (2) as free (non-co-joined) individual ligators contained on a dispersing wand, or the like, with each ligator being detachably joined integrally therewith the wand (e.g., '766 to Klein, '271 to Anderson, and '753 to Klein); (3) in elongate chains of individual, separable ligators (e.g., '033 to Klein et al. and '601 to Anderson et at.); and (4) in elongate chains of dispersing wands with each wand having free individual ligators contained on the wand (e.g., '260 to Klein).

Although anti-contamination protocols have always been important in the medical field, it seems that its importance has mushroomed with the emergence of not-yet curable, often-fatal, lingering, communicable diseases (such as AIDS) and new strains of drug-resistant, antibiotic-resistance communicable diseases. Thus, all orthodontists must strictly follow an anti-contamination protocol when dispensing intraoral tools to perform ligature operations to avoid cross-contamination. Cross-contamination may occur when an practitioner uses O-ring ligators on a patient that were previously exposed (and possibly contaminated) when the practitioner was working with on a previous patient. The need to prevent such cross-contamination from the use of O-ring ligators has been addressed in existing dispensing and handling systems, such as '033 to Klein et at.

Experienced practitioners have discovered that there are many procedures (like less-than-full-arch procedures) in which only very few ligators are required. During such procedures, it is advantageous to have a dispensing apparatus from which a practitioner may obtain a variable number of ligators. By selecting only the desired and necessary number of ligators, the practitioner is able to minimize wasteful discarding of exposed/unused ones.

Many patients wish to accentuate the existence of ligators in their mouth, rather than hide them. As a result, manufacturers of chains of cut-separable intraoral ligators produce their products in a rainbow of colors and shades. The chains typically are packaged in a color coordinating bobbin (i.e., spool). Among the colors available are various shades of red, blue, yellow, green, purple, orange, pink, cyan, magenta, etc. and also clear, black and white. Also, other types of colors are available including gold, silver, and other metallic colors.

When placing new intraoral ligators into a patient's mouth, the practitioner has a wide selection of colors from which to choose. Therefore, the practitioner needs a dispenser that is capable of dispensing plural chains of cut-separable intraoral ligators, wherein each chain may be a different color and shade.

DISCLOSURE OF THE INVENTION

The present invention provides a means of contamination-free dispensing a desired supply of cut-separable, intraoral ligators from a chain of such ligators. Preferably, the present invention also provides a means of quickly loading/unloading bobbins holding coil-wound chains of such ligators. More preferably, the present invention provides a means of easily positioning such chains into a ready-to-use position so that a user may dispense a supply of such chain.

The invented medical apparatus includes a frame and a bobbin around which a chain is wound. The chain preferably is elongate, homogeneous, and unitary and more preferably is a molded chain of plural cut-separable intraoral ligators (i.e., O-ring ligators) for use during an orthodontic ligating procedure. A hub structure and an anvil are attached to the frame. The hub structure includes a hub for mounting the bobbin thereon so that the bobbin rotates about the hub as the chain pays out from the bobbin. The anvil is attached to the frame such that the chain pays out from the bobbin in the direction toward the anvil. The anvil includes a blade and a resistance passageway through the anvil. The passageway is configured for the chain to be fed therethrough so that a section of chain may be severed from it by circumflecting the chain over the anvil and across the blade.

Preferably, the hub structure is pivotally attached to the frame so that the bobbin may be quickly loaded and unloaded from the hub. More preferably, the anvil is also pivotally attached to the frame so that the anvil can swing up to expose the resistance passageway, thereby facilitating threading of the chain through the passageway.

These and other advantages and objects of the present invention will be more readily understood after consideration of the drawings and the detailed description of the preferred embodiment which follows.

BRIEF DESCRIPTION OF THE DRAWINGS

FIG. 3 is a fragmentary, side elevation view of the dispenser of FIG. 1 with a bobbin and a swing hub structure shown in a bobbin loading/unloading position in dash-dot lines.

FIG. 4 is a fragmentary, cut-away side elevation view of a front portion of the dispenser of FIG. 1 with a rocking anvil in a chain-feeding position.

DETAILED DESCRIPTION OF THE PREFERRED EMBODIMENT AND BEST MODE FOR CARRYING OUT THE INVENTION

Figure 1:
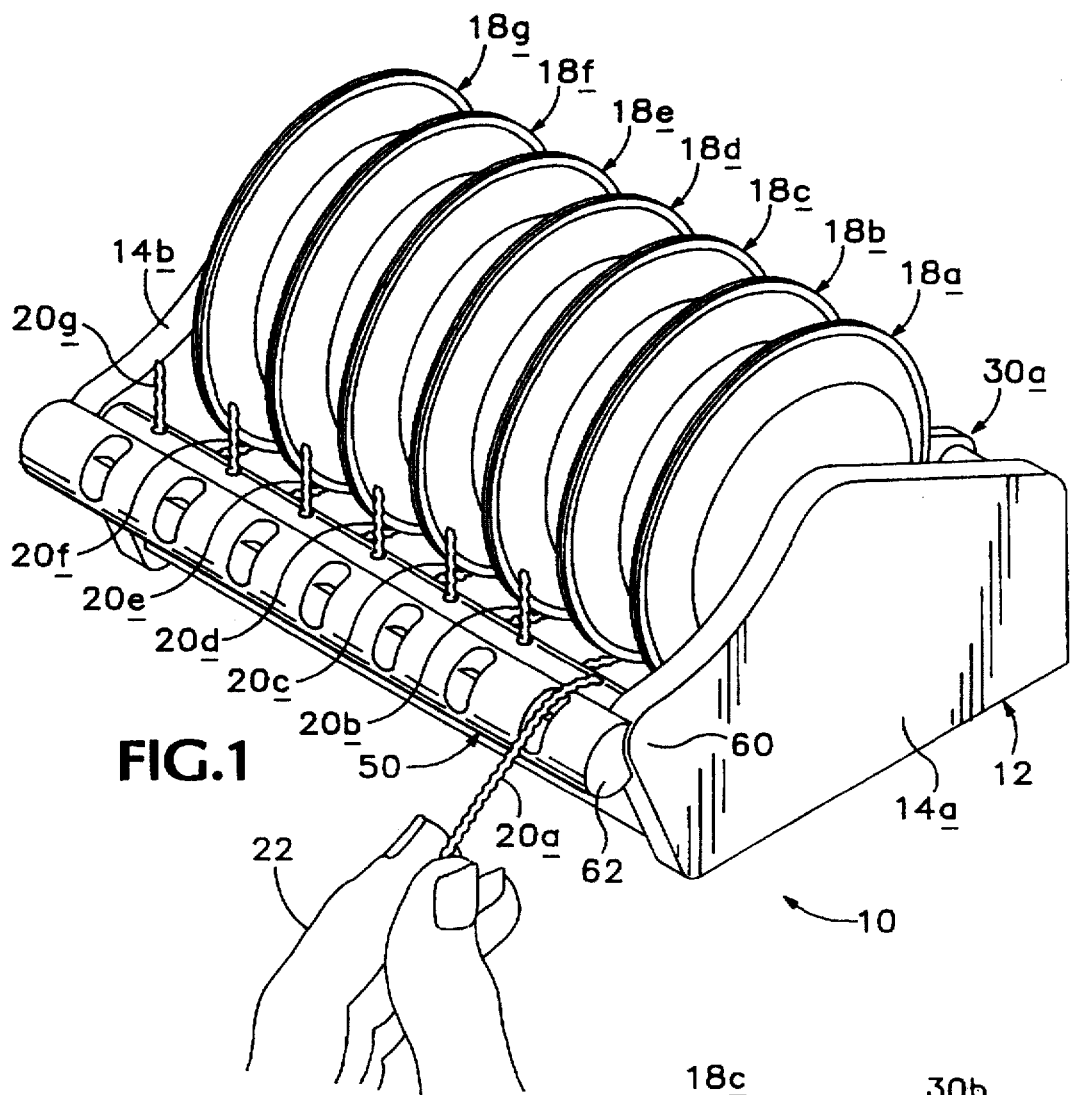
FIG. 1 is an isometric view of a chain dispenser, constructed in accordance with a preferred embodiment, showing a user's fingers pulling out a section of chain from a bobbin.

The preferred embodiment of the invented medical apparatus is shown in FIGS. 1–4, such apparatus being indicated generally at 10 in FIGS. 1 and 3. The medical apparatus includes a frame 12 having two sidewalls 14a, 14b with a floor 16 connected therebetween. Within its frame, apparatus 10 holds a plurality of bobbins 18a–18g. Preferably, the medical apparatus holds seven bobbins with each bobbin shaped approximately like a pair of cymbals lying on one another with the concave sides of the cymbals facing each another (i.e., a dual-cymbal shape). Each bobbin holds an elongate, homogeneous, unitary, elastomeric chain, which preferably is a molded chain of plural cut-separable intraoral ligators (i.e., O-ring ligators) for use during an orthodontic ligating procedure. In a ready-to-use position as shown in FIG. 1, the medical apparatus preferably presents seven chains 20a–20g, which are available for dispensing. FIG. 1 shows a user's fingers 22 grasping chain 20a, thereby to effect dispensing of a segment of the chain.

Figure 2:
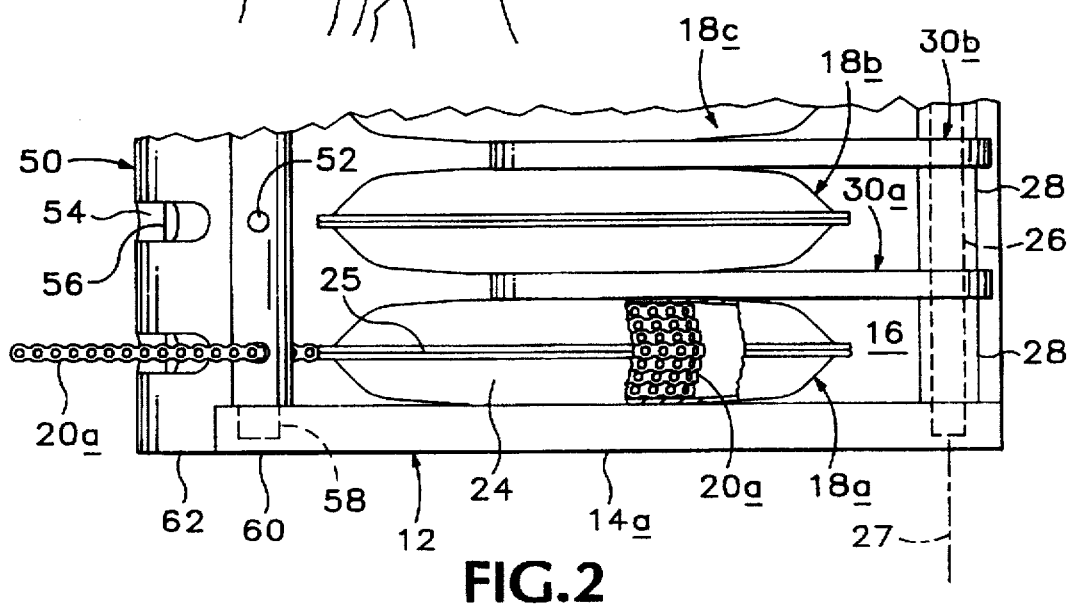
FIG. 2 is a fragmentary, top plan view of the dispenser of FIG. 1 with a bobbin cut away to reveal a chain wound within.

Each bobbin includes a casing 24 with a circular periphery. The casing forms the dual-cymbal shape of the bobbin and encloses the chain therewithin so that exposure and cross-contamination is limited. Casing 24 has a parametral, resilient, deformable lip 25 about the periphery of the casing so that as the chain pays out from the bobbin, it may escape (by slipping through the lip) the casing in a contamination-minimizing manner. Preferably, the casing is made of resilient elastomeric material so it is contained chain may easily slip through the opening between the "cymbals". FIG. 2 shows casing 24 of bobbin 18a cut away to reveal chain 20a wound about the bobbin.

As shown in FIGS. 2 and 3, medical apparatus 10 also includes a pin 26 mounted between sidewalls 14a and 14b of frame 12. All of the hub structures, for example hub structures 30a, 30b, are mounted to the frame by pin 26. A hub structure may be rigidly mounted to the frame, but it preferably is pivotally mounted to the frame via pin 26, so that a hub structure may swing about longitudinal axis 27 (shown only in FIG. 2) of the pin. A hub structure that is pivotally mounted (i.e., a swing hub structure) may be swung back and forth from a ready-to-use position to a bobbin loading/unloading position. Preferably, the medical apparatus includes a plurality of swing hub structures (e.g., swing hub structures 30a and 30b). The swing hub structure includes a sleeve 28 which is a tube surrounding the pin and connected to the swing hub structure. The sleeve allows the hub structure to rotate about pin 26 while it acts as a spacer to separate each hub structure from its neighbor hub structure or a sidewall. The length of one sleeve is preferably approximately equal to or greater than the width of the bobbin and hub.

FIG. 3 shows medical apparatus 10 with part of sidewall 14a cut away to reveal otherwise hidden structure. FIG. 3 shows swing hub structure 30a in a ready-to-use position D in solid lines and a bobbin loading/unloading position L in dash-dot lines. The swing hub structure may swing back-and-forth as indicated by arrow 31. When the chain pays out from the bobbin, the bobbin rotates. For example, in FIG. 3, bobbin 18a rotates in the direction of arrow 19 when the chain pays out; however, the bobbin may rotate in the direction opposite of arrow 19.

As shown in FIG. 3 in solid and phantom lines, each hub structure includes a substantially planar and substantially polygonal member 32. Preferably, the member is approximately the shape of a triangle with rounded corners. Member 32 has a first corner section 34 from which a hub 36 projects. Preferably, the distance that the hub projects is approximately equal to the width of the bobbin, but less than the length of sleeve 28. Each of bobbins 18a–18g includes a circular hole through its center with a diameter just slightly greater than the diameter of circular hub 36. Hub 36 has a center point 38 which is coextensive with the axis about which the bobbin rotates when a chain pays out from the bobbin. Member 32 has a second corner section 40, which has a hole therethrough that pin 26 is inserted so that the member pivots about longitudinal axis 27 of the pin to/from a ready-to-use position D from/to a loading/unloading position L. The hole of the second corner section has a center point 42 which is coincident with axis 27. The second corner's center point is at least a first predefined distance A from the hub's center point 38 so that the bobbin is free to rotate about the hub. Preferably, first predefined distance A is greater than radius R of the bobbin. Member 32 also includes a third corner section 44 having an edge 46 for supporting the member by contacting floor 16 of the frame when the member is in a ready-to-use position. Preferably, edge 46 is at least a second predefined distance B from the hub's center point 38 so that floor 16 of the frame does not interfere with the rotation of the bobbin about the hub. The second predefined distance is preferably greater than radius R of the bobbin.

As shown in FIGS. 1–4, medical apparatus 10 further includes an anvil 50 attached to frame 12 in a position relative to the hub structure such that the chains pay out from the bobbin in a direction toward the anvil. The anvil includes a plurality resistance passageways therethrough. Such a resistance passageway allows a chain to pass through the anvil, but slightly resists (i.e., interferes with) passage of the chain. Preferably, a resistance passageway allows one O-ring ligator through at a time. Preferably, the anvil includes plural such passageways. Each passageway is configured for an individual chain to be fed therethrough. The anvil also includes plural cutting recesses, such as cutting recess 54, in each of which a blade 56 is mounted. A section of chain may be severed from a chain by circumflecting the chain over the anvil and across blade 56.

Preferably, anvil 50 is pivotally attached to frame 12 by an integral peg 58 snapped into a bore in the frame for receiving such a peg. Frame 12 includes a shoulder section 60 to which the anvil is pivotally attached. The shoulder section has a convex, semicircular corner. Anvil 50 has an integral stop 62 projecting from the anvil and over shoulder section 60. The stop has a concave, semicircular recess 64 that matably conforms with the corner of shoulder section 60 such that the stop limits the extent of pivot of the anvil when boundary edges 66 of recess 64 contact the corner.

When anvil 50 is in a cutting position C (as shown in FIG. 3), the resistance passageway is substantially vertical. As shown in FIG. 4, to feed a chain through the resistance passageway, a user pivots the anvil in the direction of arrow 51 into a threading position T. In threading position T, the resistance passageway is substantially horizontal. Since the resistance passageway resists the free passage of a chain therethrough, it is difficult to initially thread the chain into and through the passageway. To facilitate threading of the chain, a stiff string 68 is inserted through an O-ring ligator at or near the end of the chain. The string acts as a needle for threading the chain through the resistance passageway.

As shown in FIG. 3, medical apparatus 10 includes an adhesion system 70 connected to the bottom of frame 12. The adhesion system is for securely adhering the frame to a surface support structure 72 so that the apparatus is immobilized. The adhesion system may also be used to connect two or more apparatuses together. Preferably, the adhesion system uses hook-and-loop fasteners.

Those who are skilled in the art will understand and appreciate that although the preferred embodiment of the invention is described as a medical apparatus for dispensing of chains of O-ring ligators, alternative embodiments may include non-medical applications and dispensing of any chain-like or string-like material. Rather being a chain of O-rings, alternative embodiments may dispense any type of chain, string, twine, cord, strand, rope, filament, wire, thread, tape, strip, ribbon, or any other string-like or chain-like material.

Industrial Applicability

The invented medical apparatus may be understood to provide an orthodontic device for dispensing a chain of intraoral O-rings for use in a ligating procedure. However, the apparatus may have other medical applications or non-medical applications. The apparatus should be helpful in facilitating the dispensing of any chain-like or string-like material.

While the preferred embodiment and best mode of the invention have been disclosed, variations and changes may be made without departing from the spirit and scope of the invention.

I claim:

1. A chain dispenser including a frame and a bobbin around which a chain is wound, the dispenser comprising:
   a swing hub structure for quick loading and unloading of the bobbin, said swing hub structure includes a hub for mounting file bobbin thereon, wherein said swing hub structure is pivotally attached to the frame and when mounted, the bobbin rotates around the hub as the chain pays out from the bobbin;
   an anvil attached to the frame such that the chain pays out from the bobbin in a direction toward said anvil, wherein said anvil includes a resistance passageway through said anvil, and carries a blade adjacent said passageway, the passageway being configured to resist the chain fed therethrough as it pays out from the bobbin so that a section of the chain is severed from the chain by circumflecting the chain over said anvil and across the blade; and
   a pin connected to a rear portion of the frame, which rear portion is opposite a front portion where said anvil is attached to the frame, wherein the frame includes a floor and said swing hub structure further includes a substantially planar and substantially polygonal member, the member having:
     a first corner section from which the hub projects, wherein the hub has a center point;
     a second corner section having a hole therethrough, wherein the pin is inserted through the hole so that the member may pivot about a longitudinal axis of the pin and swing between a ready-to-use position and a loading position and wherein the hole is at least a first predefined distance from the center point of the hub so that the hole and the pin do not interfere with rotation of the bobbin about the hub; and
     a third corner section having an edge for supporting the member on the floor of the frame when the member is in the ready-to-use position, wherein the edge is at least a second predefined distance from the center point of the hub so that the floor of the frame does not interfere with rotation of the bobbin about the hub.

2. The dispenser of claim 1 further comprising plural bobbins and hub structures, wherein said anvil includes a blade and resistance passageway corresponding to each bobbin and hub structure.

3. The dispenser of claim 1 further comprising an adhesion system connected to the frame, the adhesion system for securely adhering the frame to a surface support structure so that the dispenser is immobilized.

4. The dispenser of claim 1, wherein the bobbin is substantially circular and has a radius and wherein the first and second predefined distances are greater than the radius of the bobbin.

5. A chain dispenser including a frame and a bobbin around which a chain is wound, the dispenser comprising:
   a swing hub structure for quick loading and unloading of the bobbin, said swing hub structure includes a hub for mounting the bobbin thereon, wherein said swing hub structure is pivotally attached to the frame and when mounted, the bobbin rotates around the hub as the chain pays out from the bobbin;
   a rocking anvil pivotally attached to the frame in a position relative to said hub structure such that the chain pays out from the bobbin in a direction toward said anvil, wherein said anvil includes a blade and a resistance passageway through said anvil, the passageway configured for the chain to be fed there through so that a section of the chain is severed from the chain by circumflecting the chain over said anvil and across the blade, and wherein said anvil swings up to expose the resistance passageway, so that threading the chain through the resistance passageway is facilitated; and
   a pin connected to a rear portion of the frame, which rear portion is opposite a front portion where said anvil is attached to the frame, wherein the frame includes a floor and said swing hub structure further includes a substantially planar and substantially polygonal member, the member having: p2 a first corner section from which the hub projects, wherein the hub has a center point;
     a second corner section having a hole therethrough, wherein the pin is inserted through the hole so that the member may pivot about a longitudinal axis of the pin and swing between a ready-to-use position and a loading position and wherein the hole is at least a first predefined distance from the center point of the hub so that the hole and the pin do not interfere with rotation of the bobbin about the hub; and
     a third corner section having an edge for supporting the member on the floor of the frame when the member is in the ready-to-use-position, wherein the edge is at least a second predefined distance from the center point of the hub so that the floor of the frame does not interfere with rotation of the bobbin about the hub.

6. The dispenser of claim 5 which further comprises a plurality of bobbins and hub structures, and wherein the anvil includes, for each bobbin and hub structure, a resistance passageway, and joined to the anvil, downstream from each said additional resistance passageway, an associated blade.

7. The dispenser of claim 5 further comprising an adhesion system connected to the frame, the adhesion system for securely adhering the frame to a surface support structure so that the dispenser is immobilized.

8. The dispenser of claim 5, wherein the bobbin is substantially circular and has a radius and wherein the first and second predefined distances are greater than the radius of the bobbin.

9. The dispenser of claim 5, wherein the resistance passageway is substantially vertical when the rocking anvil is in a cutting position and the resistance passageway is substantially horizontal after the rocking anvil pivots into a chain-feeding position.

10. The dispenser of claim 5, wherein:

the frame includes a shoulder section to which said anvil is pivotally attached, the shoulder section having a convex, semi-circular corner; and said anvil includes a stop projecting from said anvil and over the shoulder section, the stop having a concave, semi-circular recess that matingly conforms with the corner of the shoulder section such that the stop limits the extent of pivot of said anvil when boundary edges of the recess contact the corner.

11. A dispenser of a chain of elongate, homogeneous, unitary, cut-separable, intraoral ligators for use during an orthodontic ligating procedure, the dispenser including a frame having a shoulder section, and the shoulder section having a convex, semi-circular corner, the dispenser comprising:

a bobbin around which the chain is wound, the bobbin including a casing with a circular periphery, wherein the casing encloses the chain therewithin so that the chain's exposure and thus cross-contamination is limited, the casing having a perimetral, resilient, deformable lip about the periphery of the casing so that as the chain pays out from the bobbin, the chain escapes the casing in a cross-contamination minimizing manner;

a swing hub structure for quick loading and unloading of the bobbin, said swing hub structure includes a hub for mounting the bobbin thereon, wherein said swing hub structure is pivotally attached to the frame and when mounted, the bobbin rotates around the hub as the chain pays out from the bobbin; and a rocking anvil pivotally attached to the shoulder section of the frame in a position relative to said hub structure and bobbin such that the chain pays out from the bobbin in a direction toward said anvil, wherein said anvil includes a blade and a resistance passageway through said anvil, the passageway configured for the chain to be fed therethrough so that a section of the chain is severed from the chain by circumflecting the chain over said anvil and across the blade, and wherein said anvil swings up to expose the resistance passageway, so that threading the chain through the resistance passageway is facilitated, said anvil including a stop projecting from said anvil and over the shoulder section, the stop having a concave, semi-circular recess that matingly conforms with the corner of the shoulder section such that the stop limits the extent of pivot of said anvil when boundary edges of the recess contact the corner.

12. The dispenser of claim 11, wherein the casing has a dual-cymbal shape with a hole therethrough for mounting onto the hub.

* * * * *